US007052704B2

(12) United States Patent
Shen et al.

(10) Patent No.: US 7,052,704 B2
(45) Date of Patent: May 30, 2006

(54) METHODS AND COMPOSITIONS FOR LIPIDIZATION OF HYDROPHILIC MOLECULES

(75) Inventors: Wei-Chiang Shen, San Marino, CA (US); Hossein M. Ekrami, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 407 days.

(21) Appl. No.: 09/845,153

(22) Filed: May 1, 2001

(65) Prior Publication Data
US 2004/0054132 A1 Mar. 18, 2004

Related U.S. Application Data

(60) Division of application No. 09/120,118, filed on Jul. 22, 1998, now Pat. No. 6,225,445, which is a division of application No. 08/524,362, filed on Sep. 5, 1995, now Pat. No. 5,907,030, which is a continuation-in-part of application No. 08/349,717, filed on Jan. 25, 1995, now abandoned.

(51) Int. Cl.
A61K 38/00 (2006.01)
A61K 39/385 (2006.01)
C07K 14/00 (2006.01)
C70H 21/00 (2006.01)

(52) U.S. Cl. .............................. 424/283.1; 424/194.1; 435/130; 530/300; 530/350; 536/22.1

(58) Field of Classification Search ................ 530/300, 530/350, 359
See application file for complete search history.

(56) References Cited

U.S. PATENT DOCUMENTS

| 5,599,903 A | 2/1997 | Kauvar et al. ............... 530/331 |
| 5,629,020 A | 5/1997 | Leone-Bay et al. .......... 424/489 |
| 5,635,380 A | 6/1997 | Naftilan et al. ........... 435/172.3 |
| 5,679,643 A | 10/1997 | Kauvar et al. ................. 514/18 |
| 5,708,146 A | 1/1998 | Willner et al. ........... 530/387.3 |
| 5,763,570 A | 6/1998 | Kauvar et al. ............... 530/331 |

FOREIGN PATENT DOCUMENTS

| EP | 0 482 766 | 4/1992 |
| JP | 63246382 | 10/1988 |
| WO | WO 90/10621 A1 | 9/1990 |
| WO | WO 91/16067 | 10/1991 |
| WO | WO 96/22773 | 8/1996 |
| WO | WO 97/49425 A1 | 12/1997 |

OTHER PUBLICATIONS

Wade, L.G. Organic Chemistry (1987) Chapter 27, pp. 1264-1265.*
Kiwada, H., et al., "Application of Synthetic Liposomes Based on Acyl Amino Acids or Acyl Peptides as Drug Carriers. I. Their Preparation and Transport of Glutathione into the Liver," *Chem. Pharm. Bull.* 35:2935-2942, Pharmaceutical Society of Japan (1987).
Supplemental European Search Report for Appl. No. EP 97 94 4483, European Patent Office, the Netherlands, completed Apr. 14, 2004.
Al-Obeidi, F., et al., "Synthesis and Biological Activities of Fatty Acid Conjugates of a Cyclic Lactam α-Melanotropin," *J. Med. Chem.* 35:118-123, American Chemical Society (1992).
Ekrami, H.M., et al., "Water-soluble fatty acid derivatives as acylating agents for reversable lipidization of polypeptides" *FEBS Lett.* 371:283-286, Elsevier Science Publishers B.V. (Sep. 1995).
European Search Report for European Patent Appl. No. 03 00 6780 mailed on Jul. 2, 2003.
Artursson, P., and Magnusson, C., "Epithelial Transport of Drugs in Cell Culture. II: Effect of Extracellular Calcium Concentration on the Paracellular Transport of Drugs of Different Lipophilicities across Monolayers of Intestinal Epithelial (Caco-2) Cells, " *J. Pharm. Sci.* 79595-600, American Pharmaceutical Association (1990).
Broadwell, R.D., et al., "Transcytotic pathway for blood-borne protein through the blood-brain barrier," *Proc. Natl. Acad. Sci. USA* 85:632-636, National Academy of Sciences (1988).
Brocklehurst, K., et al., "Preparation of Fully Active Papain From Dried Papaya Latex," *J.* 133:573-584, London Portland Press On Behalf Of The Biochemical Society (1973).
Chekhonin, V.P., et al., "Fatty acid acylated Fab-fragments of antibodies to neurospecific proteins as carriers for neuroleptic targeted delivery in brain," *FEBS Letters* 287: 149-152, Elsevier Science Publishers B. V. (1991).
Chu, Y. -C., et al., "High-Potency Hybrid Compounds Related to Insulin and Amphioxus Insulin-like Peptide," *Biochem.* 33:13087-13092, American Chemical Society (1994).
Chu, Y.-C., et al., "High-Potency Hybrid Compounds Related to Insulin and Amphioxus Insulin-like Peptide," *Chem. Abstracts* 121:212, Abstract No. 246582y. American Chemical Society (Nov. 1994).

(Continued)

*Primary Examiner*—Jon Weber
*Assistant Examiner*—Anand U. Desai
(74) *Attorney, Agent, or Firm*—Sterne, Kessler, Goldstein & Fox PLLC

(57) ABSTRACT

Fatty acid derivatives of sulfhydryl-containing compounds (for example, sulfhydryl-containing peptides or proteins) comprising fatty acid-conjugated products with a disulfide linkage are employed for delivery of the compounds to mammalian cells. This modification markedly increases the absorption of the compounds by mammalian cells relative to the rate of absorption of the unconjugated compounds, as well as prolonging blood and tissue retention of the compounds. Moreover, the disulfide linkage in the conjugate is quite labile in the cells and thus facilitates intracellular release of the intact compounds from the fatty acid moieties.

3 Claims, No Drawings

OTHER PUBLICATIONS

Conradi, R.A., et al., "The Influence of Peptide Structure on Transport Across Caco-2 Cells," *Pharm. Res.* 8:1453-1460, Plenum Publishing Corp. (1991).

Edwards, P.A.W., "Is Mucus a Selective Barrier to Macromolecules?" *British Med. Bulletin* 34:55-56, British Council, Medical Dept. (1978).

Ekrami, H.M., "Positively-charged and lipophilic Bowman-Birk Protease Inhibitor conjugates: Synthesis and Characterization of the Pharmacetical and Chemopreventive properties," A Dissertation, UMI Dissertation Services, Ann Arbor, MI, i-xiii, 9-226 (after Jan. 25, 1995).

Ekrami, H.M., et al., "Water-soluble fatty acid derivatives as acylating agents for reversible lipidation of polypeptides," *FEBS Letters* 371:283-286, Federation of European Biochemical Societies (1995).

Ekrami, H.M., et al., "Water-soluble fatty acid derivatives as acylating agents for reversible lipidization of polypeptide," *Chem. Abstracts* 124:1042, Abstract No. 30361q, American Chemical Society (1996).

Eriksson, S.A., and Mannervik, B., "A method for the direct recording of an enzyme-catalyzed thiol-disulfide interchange using mixed disulfide of glutathione and 3-carboxy-4-nitrobezenethiol," *Biochim. Biophys. Acta* 212:518-520, Elsevier Publishing Co. (1970).

Eriksson, S. and Mannervik, B., "Direct recording of an enzyme-catalyzed thiol-disulfide interchange using a mixed disulfide of glutathione and 3-carboxy-4-nitrobezenethiol," *Chem. Abstracts* 73:39, Abstract No. 127175y, American Chemical Society (1970).

Fix, J.A., et al., "Acylcarnitines: drug absorption-enhancing agents in the gastrointestinal tract," *Am. J. Physiol.* 251:G332-G340, American Physiological Society (1986).

Friden, P.M., and Walus, L.R., "Transport of Proteins Across the Blood-Brain Barrier via the Transferrin Receptor," In: Frontiers In Cerebral Vascular Biology, Transport and Its Regulation, L.R. Drewes and A.L. Betz, eds. Plenum Press New York, New York, USA. pp. 129-136 (1993).

Gonzalez-Mariscal, L., et al., "Tight Junction Formation in Cultured Epithelial Cells (MDCK), " *J. Membrane Biol.* 86:113-125, Springer-Verlag (1985).

Gordon, G.S., et al., "Nasal absorption of insulin: Enhancement by hydrophobic bile salts," *Proc. Natl. Acad. Sci. USA* 82:7419-7423, National Academy of Sciences (1985).

Hashimoto, M., et al., "Synthesis of Palmitoyl Derivatives of Insulin and Their Biological Activities," *Pharm. Res.* 6:171-176 Plenum Press (1989).

Huang, W., et al., "Lipophilic Multiple Antigen Peptide System for Peptide Immunogen and Synthetic Vaccine," *Mol. Immunol.* 31:1191-1199, Elsevier Science Ltd. (1994).

Hughes, R.A., et al., "Lipidic Peptides. III: Lipidic Amino Acid and Oligomer Conjugates of Morphine," *J. Pharm. Sci.* 80:1103-1105, American Pharmaceutical Association (1991).

Hughes, R.A., et al., "Lipidic Peptides. V: Penicillin and Cephalosporin Acid Conjugates with Increased Lipophilic Character," *J. Pharm. Sci.* 81:845-848, American Pharmaceutical Association (1992).

Inagaki, M., et al., "Macromolecular permeability of the tight junction of the human nasal mucosa," *Rhinology* 23:213-221, International Rhinologic Society (1985).

Kabanov, A.V., et al., "Lipid modification of proteins and their membrane transport," *Protein Engineering* 3:39-42, IRL Press (1989).

Kajii, H., et al., "Fluorescence Study on the Interaction of Salicylate with Rat Small Intestinal Epithelial Cells: Possible Mechanism for the Promoting Effects of Salicylate on Drug Absorption In Vivo;" *Life Sci.* 37:523-530, Pergamon Press Ltd. (1985).

Kamagami, S., et al., "Penetration enhancement across a model membrane by liposomally entrapped drugs using N,N'-diacylcystine as a bilayer lipid," Chem. Abstracts 114:457 Abstract No. 214316d, American Chemical Society (1991).

Kidron, M., et al., "The Absorption of Insulin from Various Regions of the Rat Intestine," *Life Sci.* 31:2837-2841, Pergamon Press Ltd. (1982).

Kiwada, H., et al., "Application of synthetic liposomes based on acyl amino acids or acyl peptides as drug carriers. I. Their preparation and transport of gluthathione into the liver," Chem. Abstracts 107: Abstract No. 183493h, American Chemical Society (1987).

Landolph, J.R., "Chemical Transformation in C3H 10T 1/2 C1 8 Mouse Embryo Fibroblasts: Historical Background, Assessment of the Transformation Assay, and Evolution and Optimization of the Transformation Assay Protocol," In: Transformation Assay of Established Cell Lines: Mechanisms and Application, T. Kakunaga and H. Yamasaki, eds. IARC Scientific Publications 67:185-203, International Agency for Research on Cancer (1985).

Lee, V.H.L., "Enzymatic Barriers to Peptide and Protein Absorption," *Crit. Rev. Ther. Drug Carrier Syst.* 5:69-97, CRC Press, Inc. (1988).

Lee, V.H.L., et al., "Mucosal Penetration Enhancers for Facilitation of Peptide and Protein Drug Absorption," *Crit. Rev. Ther. Drug Carrier Syst.* 8:91-192, CRC Press, Inc. (1991).

Letsinger, R.L., et al., "Cholesteryl-conjugated oligonucleotides: Synthesis, properties, and activity as inhibitors of replication of human immuodeficieny virus in cell culture," *Proc. Natl. Acad. Sci. USA* 86:6553-6556, National Academy of Sciences (1989).

Lowry, O.H., et al., "Protein Measurement with the Folin Phenol Reagent," *J. Biol. Chem.* 193:265-275, American Society of Biological Chemists, Inc. (1951).

Martins, M.B.F., et al., "Acylation of L-asparaginase with total retention of enzymatic activity," *Biochimie* 72:671-675, Elsevier Science (1990).

McConahey, P.J., and Dixon, F.J., "Radioiodination of Proteins by the Use of the Chloramine-T Method," *Meth. Enzymol.* 70:210-213, Academic Press, Inc. (1980).

Mostov, K.E., and Simister, N.E., "Transcytosis," *Cell* 43:389-390, Massachusetts Institute of Technology (1985).

Müller, C. E., et al., "Lipophilic disulfide prodrugs-syntheses and disulfide bond cleavage," *Int. J. Pharm.* 57:41-47, Elsevier Science Publishers B.V. (1989).

Muranishi, S., et al., "Lipophilic Peptides: Synthesis of Lauroyl Thyrotropin-Releasing Hormone and Its Biological Activity," *Pharm. Res.* 8:649-652, Plenum Press (1991).

Okahata, T. and Seki, T., "Functional capsule membranes, 10. pH-sensitive capsule membranes, Reversible permeability control from the dissociative bilayer-coated capsule membrane by an ambient pH change," Chem. Abstracts 102:391 Abstract No. 12733d, American Chemical Society (1985).

Reznikoff, C.A., et al., "Establishment and Characterization of a Cloned Line of C3H Mouse Embryo Cells Sensitive to Postconfluence Inhibition of Division," *Cancer Res.*

33:3231-3238, American Association for Cancer Research (1973).

Reznikoff, C.A., et al., "Quantitative and Qualitative Studies of Chemical Transformation of Cloned C3H Mouse Embryo Cells Sensitive to Postconfluence Inhibition of Cell Division," *Cancer Res.* 33:3239-3249, American Association for Cancer Research (1973).

Robert, S., et al., "Fatty Acid Acylation of RNase A using Reversed Micelles as Microreactors," *Biochem. Biophys. Res. Commun.* 196:447-454, Academic Press, Inc. (1993).

Sett, R., et al., "Macrophage-Directed Delivery of Doxorubicin Conjugated to Neoglycoprotein Using Leishmaniasis as the Model Disease," *J. Infectious Dis.* 168:994-999, The University of Chicago Press (1993).

Shen, W.-C., and Ryser, H.P.-J., "Poly (L-lysine) has different membrane transport and drug-carrier properties when complexed with heparin," *Proc. Natl. Acad. Sci. USA* 78:7589-7593, National Academy of Sciences (1981).

Shen, W.-C., et al., "Enhancement of polypeptide and protein absorption by macromolecular carriers via endocytosis and transcytosis," *Adv. Drug Delivery Rev.* 8:93-113, Elsevier Science Publishers B.V. (1992).

Smith, P.L., et al., "Oral absorption of peptides and proteins," *Adv. Drug Delivery Rev.* 8:253-290, Elsevier Science Publishers B.V. (1992).

Takaori, K., et al., "The Transport of an Intact Oligopeptide Across Adult Mammalian Jejunum," *Biochem. Biophys. Res. Comm.* 137:682-687, Academic Press, Inc. (1986).

Taub, M.E., and Shen, W.-C., "Polarity in the Transytotic Processing of Apical and Basal Membrane-Bound Peroxidase-Polylysine Conjugates in MDCK Cells," *J. Cell. Phys.* 150:283-290, Wiley-Liss, Inc. (1992).

Toth, I., "A Novel Chemical Approach to Drug Delivery: Lipidic Amino Acid Conjugates," *J. Drug Targeting* 2:217-239, Harwood Academic Publishers GmbH (1994).

Ubuka, T. et al., "Synthesis of disulfides related to glutathione and their detection in tissue," (*Ganryu Aminosan*) *Sulfur Amino Acids* 8:153-157, Ganryu Aminosan Kenkyukai (1985). [Article in Japanese].

Ubuka, T. et al., "Synthesis of disulfides related to glutathione and their detection in tissue," *Chem. Abstracts* 106:728, Abstract No. 156843v, American Chemical Society (1987).

Uchimi, I. et al., "Glutathione derivatives," *Chem. Abstracts* 73:359, Abstract No. 56440t, American Chemical Society (1970).

Uchimi, I. et al., "Glutathione derivatives," *Chem. Abstracts* 74:408, Abstract No. 54179m, American Chemical Society (1971).

Větvička, V., and Fornůsek, L., "Limitations of Transmembrane Transport In Drug Delivery," *Crit. Rev. Ther. Drug Carrier Syst.* 5:141-170, CRC Press, Inc. (1988).

Vitetta, E., "Immunotoxins: New Therapeutic Reagents for Autoimmunity, Cancer, and AIDS," *J. Clin. Immunol.* 10:15S-18S, Plenum Press (1990).

Wan, J., et al., "Transcellular Processing of Disulfide-and Thioether-Linked Peroxidase-Polylysine Conjugates in Cultured MDCK Epithelial Cells, " *J. Cell. Phys.* 145:9-15, Wiley-Liss, Inc. (1990).

Wan, J., and Shen, W.-C., "Brefeldin A and Monensin Enhance Transferrin Receptor-mediated Protein Transport across Epithelial Cells," *Pharm. Res.* 8:S-4, Plenum Press (1991).

Wan, J., et al., "Brefeldin A Enhances Receptor-mediated Transcytosis of Transferrin in Filter-grown Madin-Darby Canine Kidney Cells," *J. Biol. Chem.* 267:13446-13450, American Society for Biochemistry and Molecular Biology, Inc. (1992).

Yavelow, J., et al., "Bowman-Birk Soybean Protease Inhibitor as an Anticarcinogen," *Cancer Res.* 43:2454s-2459s, American Association for Cancer Research (1983).

Yodoya, E., et al., "Enhanced Permeability of Tetragastrin across the Rat Intestinal Membrane and Its Reduced Degradation by Acylation with Various Fatty Acids," *J. Pharm. Ex. Ther.* 271:1509-1513, American Society for Pharmacology and Experimental Therapeutics (1994).

Yoshikawa, H., et al., "Potentiation of Enteral Absorption of Human Interferon Alpha and Selective Transfer into Lymphatics in Rats," *Pharm. Res.* 5:249-250, Thieme Inc., (1985).

"Protein," In: Webster's Third New International Dictionary, Unabridged, P.B. Gove, PhD., ed. G. & C. Merriam Co. Springfield, Massachusetts, USA. p. 1823 (1971).

Patent Abstract of Japanese Publication No. 63246382, obtained from the European Patent Office.

Supplementary European Search Report of EP 96 90 3690, mailed Mar. 5, 1998.

STN Information Service: File Registry, RN 23130-02-1.

Kamagami S, et al., "Penetration enhancement across a model membrane by liposomally entrapped drugs using $N_1N'$-diacylcystine as a bilayer lipid," FEBS Lett. 281:133-136, Elsevier B.V. (1991).

Boehm, J.C. and Kingsbury, W.D., "The Use of Cysteinyl Peptides to Effect PortageTransport of Sulfhydryl-containing Compounds in *Escherichia coli*," *J. Biol. Chem.* 263:17942-17950, The American Society for Biological Chemists, Inc. (1998)

Dhanasekaran, N., et al., "Mapping of the Carboxyl Terminus within the Tertiary Structure of Transducin's a Subunit Using the Heterobifunctional Cross-linking Reagent, $^{125}$I-N-(3-Iodo-4-azidophenylpropionamido-S-(2-thiopyridyl)cysteine," *J. Biol. Chem.* 263:17942-17950, The American Society for Biological Chemists, Inc. (1988).

\* cited by examiner

METHODS AND COMPOSITIONS FOR LIPIDIZATION OF HYDROPHILIC MOLECULES

CROSS-REFERENCE TO RELATED APPLICATIONS

This application is a divisional of U.S. application Ser. No. 09/120,118, filed Jul. 22, 1998, now U.S. Pat. No. 6,225,445, which is a divisional of U.S. application Ser. No. 08/524,362, filed Sep. 5, 1995, now U.S. Pat. No. 5,907,030, which is a continuation-in-part of U.S. application Ser. No. 08/349,717, filed Jan. 25, 1995, now abandoned.

This application is a continuation-in-part of application Ser. No. 08/349,717 filed Jan. 25, 1995.

BACKGROUND OF THE INVENTION

The present invention relates generally to the fields of biology and medicine. More particularly, the present invention is directed to methods and compositions useful in increasing in mammals the absorption and retention of hydrophilic molecules, in particular peptides and proteins.

Advances in biotechnology have made possible the production of large amounts of therapeutically active and pure proteins and peptides. Currently, the therapeutic effects of most of these agents can be achieved only when they administered via invasive routes, such as by injection. Since most proteins have very short half lives, effective concentrations of these agents can be maintained only when administered by frequent injections.

Although the administration of proteins by injection is the most effective means of their delivery in vivo, patient tolerance of multiple injections is very poor. In addition, the administration of drugs via the injection routes is a skilled job and requires training; this skill and training may not always be transferable to patients. In cases where protein drugs have a life-saving role, the administration by the injection route can be accepted by the patients. However, in cases where protein drugs are just one of several possible therapies, injections of proteins and peptides are unlikely to be accepted by the patients. Therefore, alternative routes of protein and peptide delivery need to be developed.

Alternative routes of protein and peptide delivery may include the buccal, nasal, oral, pulmonary, rectal and ocular routes. Without exception, these routes are less effective than the parenteral routes of administration. However, these routes of protein and peptide delivery are still far more attractive than the parenteral routes because they offer convenience and control to the patients. The oral route is particularly attractive because it is the most convenient and patient-compliant.

Mucosal barriers, which separate the inside of the body from the outside (e.g. GI, ocular, pulmonary, rectal and nasal mucosa), comprise a layer of tightly joined cell monolayers which strictly regulates the transport of molecules. Individual cells in barriers are joined by tight junctions which regulate entry into the intercellular space. Hence, the mucosa is at the first level a physical barrier, transport through which depends on either the transcellular or the paracellular pathways [Lee, V. H. L. (1988) *CRC. Critical Rev. Ther. Drug Delivery Sys.* 5, 69–97].

Paracellular transport through water filled tight junctions is restricted to small molecules (MW<1 kDa) and is essentially a diffusion process driven by a concentration gradient across the mucosa [Lee (1988), supra; Artursson, P., and Magnusson, C. (1990) *J. Pharm. Sci.* 79, 595–600]. The tight junctions comprise less than 0.5% of the total surface area of the mucosa [Gonzalez-Mariscal, L. M. et al. (1985) *J. Membrane. Biol.* 86, 113–125; Vetvicka, V., and Lubor, F. (1988) *CRC Critical Rev. Ther. Drug Deliv. Sys.* 5, 141–170]; therefore, they play only a minor role in the transport of protein drugs across the mucosa.

The transcellular transport of small drugs occurs efficiently provided the physiochemical properties of the drug are suited to transport across hydrophobic cell barriers. However, the transcellular transport of proteins and peptides is restricted to the process of transcytosis [Shen, W. C. et al. (1992) *Adv. Drug Delivery Rev.* 8, 93–113]. Transcytosis is a complex process in which proteins and peptides are taken up into vesicles from one side of a cell, and are subsequently shuttled through the cell to other side of the cell, where they are discharged from the endocytic vesicles [Mostov, K. E., and Semister, N. E. (1985) *Cell* 43, 389–390]. The cell membrane of mucosal barriers is a hydrophobic lipid bilayer which has no affinity for hydrophilic, charged macromolecules like proteins and peptides. In addition, mucosal cells may secrete mucin which can act as a barrier to the transport of many macromolecules [Edwards, P. (1978) *British Med. Bull.* 34, 55–56]. Therefore, unless specific transport mechanisms exist for protein and peptide, their inherent transport across mucosal barriers is almost negligible.

In addition to providing a tight physical barrier to the transport of proteins and peptides, mucosal barriers possess enzymes which can degrade proteins and peptides before, after, and during their passage across the mucosa. This barrier is referred to as the enzymatic barrier. The enzymatic barrier consists of endo- and exopeptidase enzymes which cleave proteins and peptides at their terminals or within their structure. Enzymatic activity of several mucosa have been studied and the results demonstrated that substantial protease activity exists in the homogenates of buccal, nasal, rectal and vaginal mucosa of albino rabbits and that these activities are comparable to those present in the ilium [Lee et al. (1988), supra]. Therefore, regardless of the mucosa being considered, the enzymatic barrier present will feature strongly in the degradation of the protein and peptide molecules.

The N and the C termini of peptides are charged and the presence of charged side chains impart highly hydrophilic characteristics on these macromolecules. In addition, the presence of charged side chains means that proteins and peptides have strong hydrogen binding capacities; this H-binding capacity has been demonstrated to play a major role in inhibiting the transport of even small peptides across cell membranes [Conradi, R. A. et al. (1991) *Pharm. Res.* 8, 1453–1460]. Therefore, the size and the hydrophilic nature of proteins and peptides combine to severely restrict their transport across mucosal barriers.

One approach that has been used to alter the physical nature of the mucosal barriers is the use of penetration enhancers. The use of penetration enhancers is based on the disruption of the cell barriers by the use of low molecular weight agents which can fluidize cell membranes [Kaji, H. et al. (1985) *Life Sci.* 37, 523–530], open tight junctions [Inagaki, M. et al. (1985) *Rhinology* 23, 213–221], and create pores in the cell membrane [Gordon, S. et al. (1985) *Proc. Natl. Acad. Sci. USA* 82, 7419–7423; Lee, V. H. L. et al. (1991) *Critical Reviews in Therapeutic Drug Carrier Systems, CRC Press* 8, 91–192]. The use of these agents leads to a non-specific loss of barrier integrity and can lead to the absorption of a variety of large molecules which can be toxic to cells in vivo.

Protease inhibitors have been co-administered with proteins and peptides and have shown some limited activity in enhancing the absorption of these macromolecules in vivo [Kidron, M. et al. (1982) *Life Sci.* 31, 2837–2841; Takaroi, K. et al. (1986) *Biochem. Biophys. Res. Comm.* 137, 682–687]. The safety and the long term effects of this approach have yet to be thoroughly investigated.

The prodrug approach is based on the modifications of peptides in a manner that will protect them from enzyme degradation and recognition. This has been achieved by substitution of the D-forms of amino acids in the structure of peptides, the blockage of vulnerable groups on peptides by amidation and acylation, the inversion of the chirality of peptides, and the introduction of conformational constraints in the peptide structure. The synthesis of prodrugs is only applicable to small peptides which have easily identifiable domains of activity.

Reduction in size is another feasible approach to increasing the transport potential of proteins. However, the active sites of proteins need to be mapped before size reduction can be attempted. In general, this approach is difficult to apply to the majority of proteins.

Carrier ligands, by virtue of their properties, can alter the cell uptake and transport characteristics of proteins and peptides. The essence of this approach is that a cell-impermeant protein or peptide is covalently attached to a carrier which is highly transported into cells. The mechanisms through which carrier ligands become endocytosed and transcytosed are important in deciding the suitability of the carrier for enhancing the transport of proteins and peptides. Macromolecular carriers are hydrophilic and do not partition into the membrane. Therefore, the transport of large polymeric carriers into the cells is mediated by the affinity of the carrier for the cell membrane. Generally, the uptake of a macromolecular conjugate starts with the binding to the cell membrane. The binding of the carrier to the cells can be specific (e.g. binding of antibodies to cell surface antigens), nonspecific (binding of cationic ligands or lectins to cell surface sugars), or receptor mediated (binding of transferrin or insulin to their receptors). Once the carrier is bound to the cell surface, it is taken up into vesicles. These vesicles then become processed stepwise and can be routed to several pathways. One pathway is the recycling of the vesicle back to the membrane from which it was invaginated. Another pathway, which is destructive to the conjugate, is the fusion with lysosomes. An alternative pathway, and one which leads to the transcytosis of the conjugate, is the fusion of the vesicle with the membrane opposite to the side from which it was derived.

The correct balance between the processes of endocytosis and transcytosis determine the delivery of a protein conjugate to its target. For instance, endocytosis may determine the extent to which a conjugate is taken up by the target cell, but transcytosis determines whether or not a conjugate reaches its target [Shen et al. (1992), supra]. For successful absorption through the GI-tract, a conjugate must bind the apical membrane of the GI-mucosa, become internalized into the mucosal cells, be delivered across the cells, and finally become released from the basolateral membrane.

The current literature contains many reports which demonstrate that nonspecific carriers, such as polylysines [Shen, W. C., and Ryser, H. J. P. (1981) *Proc. Natl. Acad. Sci. USA* 78 7589–7593] and lectins [Broadwell, R. D. et al. (1988) *Proc. Natl. Acad. Sci. USA* 85, 632–646], and specific carriers, such as transferrin [Wan, J. et al. (1992) *J. Biol. Chem.* 267, 13446–13450], asialoglycoprotein [Seth, R. et al. (1993) *J. Infect. Diseases* 168, 994–999], and antibodies [Vitetta, E. S. (1990) *J. Clin. Immunol.* 10, 15S–18S] can enhance the endocytosis of proteins into cells. Reports dealing with transcytotic carriers for proteins are fewer, and very few studies have quantitated the transport of protein conjugates across cell barriers. Wheat germ agglutinin [Broadwell et al. (1988), supra] and an anti-transferrin/methotrexate conjugate [Friden, P. M., and Walus, L. R. (1993) *Adv. Exp. Med. Biol.* 331, 129–136] have been shown to be transcytosed across the blood brain barrier in vivo. Also, polylysine conjugates of horseradish peroxidase (HRP) and a transferrin conjugate of HRP have been shown to be transcytosed across cell monolayers in vitro [Wan, J. and Shen, W. C. (1991) *Pharm. Res.* 8, S-5; Taub, M. E., and Shen, W. C. (1992) *J. Cell. Physiol.* 150, 283–290; Wan, J. et al. (1992) *J. Biol. Chem.* 267, 13446–13450, supra].

Fatty acids, as constituents of phospholipids, make up the bulk of cell membranes. They are available commercially and are relatively cheap. Due to their lipidic nature, fatty acids can easily partition into and interact with the cell membrane in a non-toxic way. Therefore, fatty acids represent potentially the most useful carrier ligands for the delivery of proteins and peptides. Strategies that may use fatty acids in the delivery of proteins and peptides include the covalent modification of proteins and peptides and the use of fatty acid emulsions.

Some studies have reported the successful use of fatty acid emulsions to deliver peptide and proteins in vivo [Yoshikawa, H. et al. (1985) *Pharm. Res.* 2, 249–251; Fix, J. A. et al. *Am. J. Physiol.* 251, G332–G340]. The mechanism through which fatty acid emulsions may promote the absorption of proteins and peptides is not yet known. Fatty acid emulsions may open tight junctions, solubilize membranes, disguise the proteins and peptides from the GI environment, and carry proteins and peptides across the GI-mucosa as part of their absorption [Smith, P. et al. (1992) *Adv. Drug Delivery Rev.* 8, 253–290]. The latter mechanism has been proposed, but is inconsistent with current knowledge about the mechanism of fat absorption.

A more logical strategy to deliver proteins and peptides across the GI-epithelium is to make use of fatty acids as non-specific membrane adsorbing agents. Several studies have shown that a non-specific membrane binding agent linked to a protein can promote the transcytosis of a protein conjugate across cells in vitro [Wan, J. et al. (1990) *J. Cell. Physiol.* 145, 9–15; Taub and Shen (1992), supra]. Fatty acid conjugation has also been demonstrated to improve the uptake of macromolecules into and across cell membranes [Letsinger, R. et al. (1989) *Proc. Natl. Acad. Sci. USA* 86, 6553–6556; Kabanov, A. et al. (1989) *Protein Eng.* 3, 39–42]. Nonetheless, there have been difficulties in conjugating fatty acids to peptides and proteins, including: (1) the lack of solubility of fatty acids in the aqueous solution for the conjugation reaction; (2) the loss of biological activity of peptides and proteins after fatty acid acylation; and (3) the lack of solubilitty of fatty acid-conjugated peptides in aqueous solutions [see, e.g., Hashimoto, M. et al., *Pharm. Res.* 6, 171–176 (1989); Martins, M. B. F. et al., *Biochimie* 72, 671–675 (1990); Muranishi, S. et al., *Pharm. Res.* 8, 649–652 (1991); Robert, S. et al., *Biochem. Biophys. Res. Commun.* 196, 447–454 (1993)].

It is an object of the present invention to provide methods and compositions for use in conjugating fatty acids to hydrophilic molecules and in improving the bioavailability of peptides and proteins.

SUMMARY OF THE INVENTION

In accordance with the present invention, fatty acid derivatives of sulfhydryl-containing compounds (for example, peptides, proteins or oligonucleotides which contain or are modified to contain sulfhydryl groups) comprising fatty acid-conjugated products with a disulfide linkage are employed for delivery of the sulfhydryl-containing compounds to mammalian cells. This modification markedly increases the absorption of the compounds by mammalian cells relative to the rate of absorption of the unconjugated compounds, as well as prolonging blood and tissue retention of the compounds. Moreover, the disulfide linkage in the conjugate is quite labile in the cells and thus facilitates intracellular release of the intact compounds from the fatty acid moieties. Reagents and methods for preparation of the fatty acid derivatives are also provided.

DETAILED DESCRIPTION OF THE INVENTION

Pursuant to the present invention, a sulfhydryl-containing compound (for example, a biopolymer as hereinafter defined) is attached to a fatty acid derivative via a reversible, biodegradable disulfide bond. Such a conjugate would be expected to bind to the apical side of a cell membrane, reach the basolateral membrane of the GI-epithelium as a result of membrane transport and turnover, and become released into interstitial fluid as the result of disulfide bond reduction.

Pursuant to one aspect of the present invention, there are provided conjugates of the general formula VI

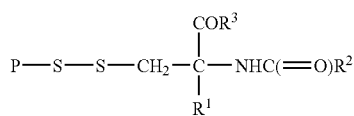

in which P is a residue derived from a sulfhydryl-containing compound; $R^1$ is hydrogen, lower alkyl or aryl; $R^2$ is a lipid-containing moiety (as hereinafter defined); and $R^3$ is —OH, a lipid-containing moiety or an amino acid chain comprising one or 2 amino acids and terminating in —$CO_2H$ or —$COR^2$. These conjugates are particularly useful for increasing the absorption and prolonging blood and tissue retention of the sulfhydryl-containing compound PSH.

Pursuant to another aspect of the present invention, methods for increasing the absorption or prolonging blood and tissue retention in a mammal of a sulfhydryl-containing compound of the general formula PSH are provided, in which a conjugate of general formula VI is formed from the sulfhydryl-containing compound and the conjugate is then administered to the mammal (for example, in an aqueous solution or an oral dosage unit).

Pursuant to yet another aspect of the present invention, there are provided compounds of the general formula V $$A\text{-}S\text{—}S\text{—}CH_2\text{—}CR^1(NHCOR^2)C(\text{=}O)R^3 \qquad V$$

in which A is an aromatic activating residue (as hereinafter defined) and $R^1$, $R^2$ and $R^3$ are as previously defined. The compounds of general formula V are particularly useful in preparation of conjugates of general formula VI from sulfhydryl-containing compounds of general formula PSH.

Pursuant to still another aspect of the present invention, there are provided method for forming conjugates of general formula VI from sulfhydryl-containing compounds of general formula PSH, which comprises reacting a compound of general formula PSH with a compound of general formula V. The reaction is typically carried out with an excess (e.g., a two-fold to a ten-fold excess) of the compound of general formula V for a period of time of about 1 hour to about 24 hours at a temperature of about 4° C. to about 37° C. in a suitable aqueous buffer solution (e.g., phosphate, bicarbonate and borate buffers). Preferably, the reaction is carried out in bicarbonate buffer, pH 8.

Pursuant to another aspect of the present invention, there are provided compounds of the general formula III $$A\text{-}S\text{—}S\text{—}CH_2\text{—}CR^1(NH_2)C(\text{=}O)R^{3'} \qquad III$$

in which $R^{3'}$ is —OH or an amino acid chain comprising one or two amino acids and terminating in —$CO_2H$ and A and $R^1$ are as previously defined. The compounds of general formula III are useful in preparing the compounds of general formula V. The compounds of general formula III are suitably prepared by reacting a compound of general formula II $$H\text{—}S\text{—}CH_2\text{—}CR^1(NH_2)C(\text{=}O)R^{3'} \qquad II$$

with a compound of general formula A-S—S-A or A-S—S-A', in which A' is different from A and is an aromatic activating residue. These reactants are either commercially available [e.g., 2,2'-dithiopyridine and 5,5'-dithiobis(2-nitrobenzoic acid)] or may be prepared by routine synthetic procedures well known to those skilled in the art.

Pursuant to still another aspect of the present invention, there are provided methods for preparation of compounds of general formula V in which $R^2$ is a lipid group, wherein a compound of general formula III is reacted with an activated lipid group of general formula X—$O_2C$—B or X—OC—B, in which X is a lipid-activating group (as hereinafter defined) and B is a lipid group (as hereinafter defined). Compounds of general formula X—$O_2C$—B or X—OC—B may be readily prepared in a manner known per se.

For preparation of a compound of general formula III, in an exemplary procedure generally equal molar quantities of a compound of general formula II and a compound of formula A-S—S-A or A-S—S-A' may suitably be mixed in a polar organic solvent (e.g., ethanol). The product of general formula III may then suitably be isolated by crystallization from a nonpolar organic solvent (e.g., benzene). Of course, other suitable procedures would also be evident to those working in the field.

For preparation of X—$O_2C$—B or X—OC—B, a fatty acid may for example be reacted with: (a) N-hydroxysuccinimide and a carbodiimide reagent to form an H-hydroxysuccinimidyl active ester; (b) trifluoroacetic anhydride to form a fatty acid anhydride; or (c) thionyl chloride to form a fatty acid chloride. Alternative procedures may also suitably be employed to introduce these or other lipid-activating groups.

For purposes of the present invention, the term "lipid-containing moiety" refers to either a lipid group per se or a hydrocarbon-based group (in particular, one or more amino acids) comprising a lipid group. By the term "lipid group" is meant a hydrophobic substituent comprising about 4 to about 26 carbon atoms, preferably about 5 to about 19 carbon atoms. Suitable lipid groups include, but are not limited to, the following: palmityl ($C_{15}H_{31}$); oleyl ($C_{15}H_{29}$); stearyl ($C_{17}H_{35}$); cholate; and deoxycholate.

By "aromatic activating residue" is meant a moiety which serves to make the disulfide group of the compounds of general formula V more labile to the displacement reaction with the sulfhydryl-containing compounds of general formula PSH (and thus, serves as a good leaving group). A presently preferred aromatic activating group is 2-pyridyl; other suitable aromatic activating groups include 4-nitrophenyl.

The term "lipid-activating group" refers for purposes of the present invention to a moiety which renders a carboxy-lipid group to which it is attached reactive with a compound of general formula III. A presently preferred lipid-activating group is N-hydroxysuccinimidyl ester; other suitable lipid-activating groups include acid chloride and acid anhydride.

While the present invention contemplates the preparation and use of conjugates of general formula VI comprising a wide range of compounds containing sulfhydryl groups, it is particularly advantageous to employ the methods and compositions of the present invention for preparation of conjugates comprising biopolymers. Biopolymers of interest include peptides, proteins, and oligonucleotides (as hereinafter defined). As would be readily apparent to those working in the field. biopolymers or thiolated biopolymers containing sulfhydryl groups may comprise a plurality of moieties corresponding in structure to the conjugates of general formula VI (i.e., groups having the structure of the compounds of general formula VI minus the moiety P).

For purposes of the present invention, the term "peptide" refers to amino acid chains comprising two to 50 amino acids and the term "protein" to amino acid chains comprising more than 50 amino acids. The proteins and peptides may be isolated from natural sources or prepared by means well known in the art, such as recombinant DNA technology or solid-state synthesis. It is contemplated that the peptides and proteins used in accordance with the present invention may comprise only naturally-occurring L-amino acids, combinations of L-amino acids and other amino acids (including R-amino acids and modified amino acids), or only amino acids other than L-amino acids. In order to form a conjugate of general formula I, the peptide or protein must bear at least one reactive thiol group. In many cases, the peptide or protein contains cysteine residues (an amino acid comprising a thiol group). A peptide or protein which does not contain a thiol group may be modified by procedures well known per se to those working in the field; in particular, well known thiolating agents [e.g., N-succinimidyl-3-(2-pyridyldithio)propionate (SPDP) and 2-iminothiolane (Traut's reagent)] may be routinely employed for this purpose.

The term "oligonucleotide" refers to chains comprising two or more naturally-occurring or modified nucleic acids, for example naturally-occurring or recombinant deoxyribonucleic acids (DNA) and ribonucleic acid (RNA) sequences. For formation of a conjugate in accordance with the present invention, the oligonucleotide must be modified by thiolating reactions so as to contain a sulfhydryl group for linking with the lipid-containing moiety. Such modifications may be routinely carried out in a manner known per se. For example, an oligonucleotide may be coupled to cystamine using carbodiimide and subsequently reduced by dithiothreitol to generate a free sulfhydryl group.

In one preferred class of compounds of general formula VI, $R^1$ is hydrogen, $R^2$ is a lipid moiety and $R^3$ is —OH. This type of conjugate is suitably derived from cysteine. In another preferred class of conjugate in accordance with the present invention, $R^1$ is hydrogen, $R^2$ is —CH$_2$CH$_2$CH(NH$_2$)CO$_2$H or —CH$_2$CH$_2$CH(NHCO-lipid)CO-lipid and $R^3$ is —NHCH$_2$CO$_2$H or —NHCH$_2$CO-lipid in which at least one of $R^2$ and $R^3$ comprises a lipid moiety. This type of conjugate is suitably derived from glutathione.

The synthesis of an exemplary compound of general formula VI (in which P is a protein) is illustrated in Scheme I. Of course, as would be readily appreciated by those skilled in the art, a variety of alternative synthetic schemes could also readily be developed.

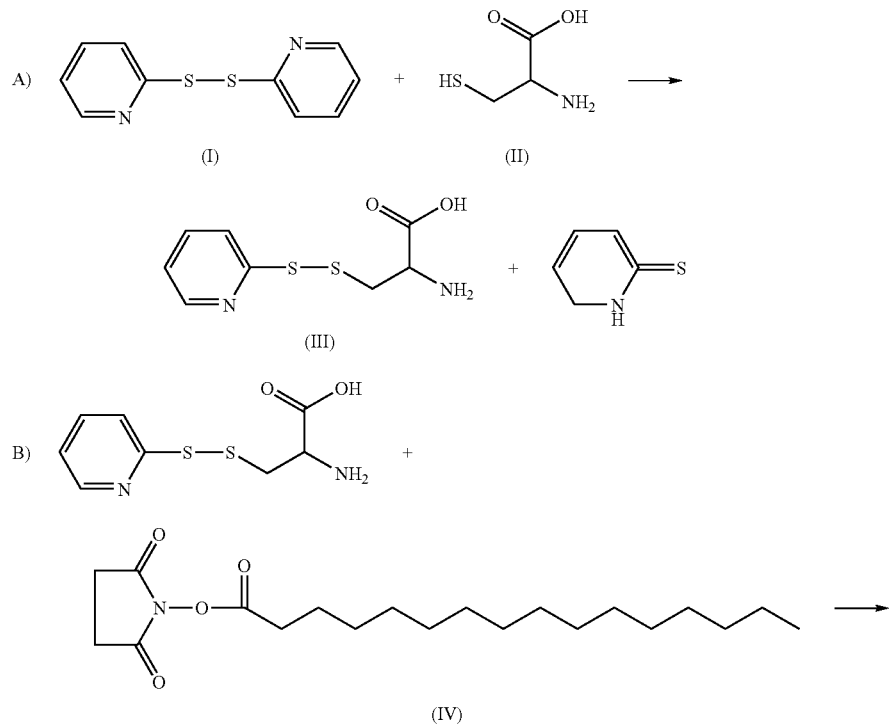

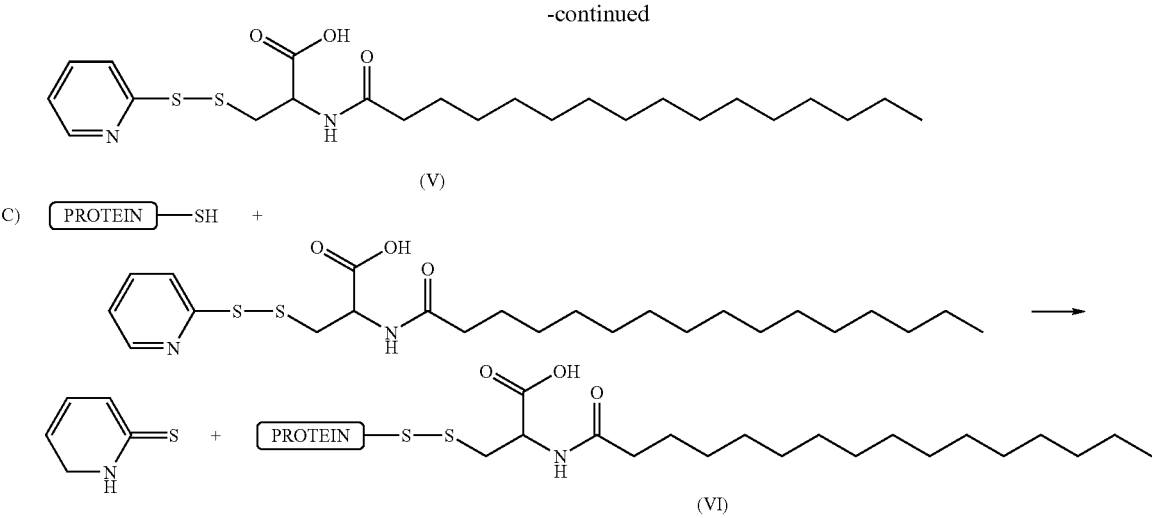

The fatty acid conjugates of the present invention are soluble in most buffer solutions in which proteins and peptides are soluble. In particular, any free carboxylic acid groups are charged at neutral pH and therefore improve the solubility of the conjugates. This greatly facilitates the formulation of the conjugates with suitable pharmaceutically-acceptable carriers or adjuvants for administration of the proteins or peptides to a patient by oral or other routes.

It is a particular advantage in accordance with the present invention that the disulfide linkage between the fatty acid moiety and the peptide or protein may readily be reduced. Therefore, the active peptide or protein molecules are released in intact form inside the target tissues or cells. Furthermore, the fatty acid moiety of the conjugates comprises only amino acids and lipid molecules which are not toxic to mammals, in particular humans.

The invention may be better understood with reference to the accompanying examples, which are intended for purposes of illustration only and should not be construed as in any sense limiting the scope of the invention as defined in the claims appended hereto.

EXAMPLES

Example 1

Synthesis of N-palmityl-2-pyridyldithiocysteine (Pal-PDC)

An ice-cold solution of L-cysteine (I) (3.0 g) in ethanol (50 ml) was added dropwise to a stirred solution of 2,2-dithiopyridine (II) (7.5 g) in ethanol (30 ml), and the reaction was allowed to proceed at 25° C. for 18 hr. The solution was centrifuged in order to remove any precipitate, and the supernatant was reduced in volume to 40 ml using a rotary evaporator. Subsequently, the reaction mixture was added dropwise to 400 ml of ice-cold benzene. PDC (III), which crystallized in benzene, was isolated by filtration, redissolved in 40 ml of ethanol, and then recrystallized in 400 ml of ice-cold benzene as described above. The recrystallized product was isolated by filtration, dried under vacuum overnight, and finally stored at −20° C. in a desiccator.

PDC (100 mg) (III) was dissolved in 5 ml of DMF and mixed with 100 µl of triethylamine, and the resultant suspension was reacted with the N-hydroxysuccinimide ester of palmitic acid (IV) (250 mg) in DMF (5 ml) at 25° C. for 24 hr, during which time the suspension turned clear. This solution was diluted with 40 ml of ice-cold water, pH 3.0, and the precipitate, which contained Pal-PDC (V) and palmitic acid, was isolated by centrifugation at 10000 rpm for 30 min. Pal-PDC (V) was separated from palmitic acid by suspension of the precipitate in water, pH 7.0, which dissolved Pal-PDC (V), but not palmitic acid. Pal-PDC (V) was purified further using two more steps of acid precipitation as described above.

Example 2

Synthesis of Conjugates

Unless otherwise stated, all the final reagents used in the conjugation steps (Pal-PDC and PDC) were analyzed using silica-coated thin layer chromatography (TLC) plates containing fluorescent indicators. These plates were not activated by heating prior to any of the analyses. For the routine analysis of the reagents synthesized, 5 µl of a ethanolic solution containing the reagent (5 mg/ml) was applied to the plates. Subsequently, the plates were developed in solvent chambers, equilibrated with the mobile phase. Once the solvent front had travelled a sufficient distance, the plates were removed, dried, and studied under a UV-lamp. Positions of the spots were marked on the plates immediately, and a drawing of the plate and the spots was made. The Rf value for each spot visualized was calculated and recorded. The composition of the mobile phases used in the analyses were adjusted to provide optimum separation of the reagent-spots.

For purposes of illustration, conjugates of BBI were synthesized. BBI is a hydrophilic protein which has low uptake into cells and is not orally bioavailable. In addition, BBI is stable in the GI tract and resists degradation by the mammalian proteases in the gut [Yavelow, J. et al. (1983) Cancer. Res. 43, 2454s–2459s]. The use of BBI for chemoprevention can be accepted only if an orally absorbable form of BBI can be developed.

BBI (20 mg) was dissolved in 1 ml of a sodium bicarbonate solution (0.3 M, pH 8.0) and reacted with SPDP (5 mg/100 µl of DMF) for 2 hr at 25° C. After purification of BBI-PDP using Sephadex® G50 gel-filtration chromatography, the PDP-derivatization of BBI was estimated by measuring the release of the thiopyridine moiety after reduction of BBI-PDP with dithiothreitol (DTT). Using this procedure, approximately 4 amino groups per BBI molecule were modified with SPDP. The level of derivatization of BBI could be controlled by adjusting the pH of the reaction buffer; the modification of BBI could be adjusted from one amine group per BBI molecule when the reaction was carried out at pH 7, to 4.5 amine groups modified when the reaction was carried out at pH 8.5.

BBI-PDP (20 mg) in PBS (1 ml, pH 5.0) was reduced with DTT (25 mM) for 30 min and subsequently eluted from a Sephadex® G50 column. The sulfhydryl-containing BBI fractions, which eluted at the column void volume, were identified using Elman's reagent, and then reacted with a 3-fold excess (per sulfhydryl group on BBI) of Pal-PDC (V) in PBS, pH 7.0, for 16 hrs at 4° C. The reaction mixture was then acidified to pH 3.0 using HCI (1M) and left on ice for 30 min. The supernatant was analyzed separately using a Sephadex G25 gel-filtration column. The precipitate, which contained the palmityl disulfide conjugate of BBI, BBIssPal (VI), and the excess reagent, was isolated by centrifugation, dissolved in DMF (2 ml), and eluted from a Sephadex® LH20 column using DMF. BBIssPal (VI) fractions, which eluted at column void volume, were isolated, dialyzed 3 times against 500 volumes of water, and then lyophilized. The yield of the conjugate using this procedure was approximately 80% (by weight). The conjugation of Pal-PDC to BBI was confirmed and quantitated after the conjugation of [3H]-labeled Pal-PDC (V) to BBI using identical conjugation conditions as the ones described above. Also, using an identical procedure, the oleic acid conjugated BBI (BBIssOleic) was synthesized.

Example 3

Transport of Conjugates

Human colon carcinoma cells (Caco-2) were detached from 25 cm$^2$ stock culture flasks using a 10 min incubation at 37° C. with 0.5 ml of a trypsin/EDTA solution (0.5% trypsin, 5.3 mM EDTA). The cells were then suspended in 5 ml of Dulbecco's minimum essential medium, supplemented with 15% fetal bovine serum (FBS), L-glutamine (1%), and essential amino acids (1%), and counted using a coulter counter.

Suspended Caco-2 cells in 1.5 ml of medium were seeded into the apical chamber of the transwells at a density of 0.5 million cells per insert. 2.5 ml of the medium was then added to the basal chambers of each transwell. The cells were allowed to attach for 2 days without disturbance and were then fed every other day until the experiments were performed. The cells were maintained for approximately 14–20 days prior to the experiments and were fed 24 hr before each experiment. The cell monolayers developed a transepithelial electrical resistance (TEER) of approximately 500–600 $\Omega cm^2$ within one week of the seeding and maintained this resistance for up to 21 days post-seeding.

Radioiodination of BBI and BBIssPal was carried out using the chloramine-T method [McConahey, P. C., and Dixon, F. J. (1980) *Meth. Enzymol.* 70, 221–247]. Confluent, 14-day old cell monolayers were washed once with, and then incubated in, serum-free Dulbecco medium at 37° C. for 30 min. Subsequently, the incubation medium was replaced with serum free medium containing $^{125}$I-BBI (10 µg/ml), either as native-BBI or as BBIssPal or BBIssOleic, and the monolayers were incubated for a further 60 min at 37° C. The monolayers were then washed three times with ice-cold PBS, and then exposed to trypsin (0.5%, EDTA 5.3 mM) for 10 min at 37° C. The detached cells were transferred to tubes, isolated by centrifugation, washed three times using ice-cold PBS, assayed for accumulated radioactivity using a gamma counter, and finally assayed for cell protein using the published method [Lowry, O. H. et al. (1951) *J. Biol. Chem.* 193, 265–275].

In some experiments the uptake of reduced $^{125}$I-BBIssPal into cells was determined. $^{125}$I-BBIssPal was reduced with DTT (50 mM) at 60° C. for 5 min followed by a further 25 min at 37° C. In control experiments, $^{125}$I-BBIssPal was exposed in medium to the same temperatures without being exposed to DTT.

The uptake of $^{125}$I-BBIssPal in the presence of BSA (fatty acid free) was determined as follows. $^{125}$I-BBIssPal was incubated with medium containing 0.1% BSA for 30 min at 37° C. before being added to the cell monolayers. In some uptake experiments, BSA was first mixed with a 3 fold molar excess of palmitic acid, and then incubated with the conjugates prior to the experiments. In the experiments where the uptake of $^{125}$I-BBIssPal was determined in medium containing FBS, the conjugates was simply added to the medium containing the required amount of FBS.

Confluent cell monolayers, 2 to 3 weeks old, and having a TEER value of approximately 500 $\Omega cm^2$, were first incubated with Dulbecco's MEM containing 1% of FBS for 30 min at 37° C. Subsequently, the incubation medium was removed, and the $^{125}$I-BBI (10 µg/ml) conjugates in 1.5 ml of the medium was added to the apical chamber of the transwells. To the basal chamber, 2.5 ml of the medium was added and the transwells were incubated at 37° C. At predetermined times, the entire basal chamber medium (2.5 ml) from each transwell was removed and counted for radioactivity using a gamma counter. In each experiment, typically seven samples were taken at 1, 2, 3, 4, 5, 6 and 24 hr post-incubation. After the 24 hr samples were taken, the cell monolayers were rinsed three times with ice-cold PBS, cut out of the inserts, and counted for accumulated radioactivity using a gamma counter.

The integrity of the $^{125}$I-BBI conjugates transported across the monolayers was studied using Sephadex G50 gel-filtration chromatography. Briefly, after the basal medium was sampled at 24 hr, 1.0 ml of the medium was centrifuged at 2000 rpm and then eluted from a G50 column (10 ml) using PBS; 1 ml fractions were collected and the fraction-associated radioactivity was determined using a gamma counter. Intact conjugates eluted at column void volume and fragments smaller than 1 kDa were eluted at or above the column volume.

The results of the uptake of $^{125}$I-BBI, either as the free protein or in conjugated form to palmitic acid, in the presence of different amounts of added FBS are shown in Table 1. When the conjugates were incubated with the cells in serum-free medium, the uptake of BBIssPal was approximately 140-fold higher than that of BBI. In the presence of medium containing 1% FBS, the internalization of BBIssPal was increased by 35-fold over that of BBI. Increasing the serum concentration further to 10%, caused a further decrease in the uptake of BBIssPal into the cells to only a 10-fold higher level than that of native-BBI. The internalization of BBIssPal into Caco-2 cells was reduced drastically in the presence of serum to 14% and 2.3% of that of the serum-free values for 1% and 10% FBS containing media, respectively.

TABLE 1

| | Uptake (ng BBI/mg of cell protein)/hr | | |
|---|---|---|---|
| | serum free | 1% FBS | 10% FBS |
| BBI | 3.9 ± 0.19 | 2.2 ± 0.17 | 1.3 ± 0.02 |
| BBIssPal | 540.0 ± 24.13 | 78.5 ± 3.41 | 12.9 ± 0.02 |

The cell monolayers were incubated with 125I-labeled conjugates at 10 μg/ml for 60 min at 37° C. The results presented are the average of three monolayers ± SEM. The uptake experiments were carried out in Dulbecco medium, in the presence and absence of added FBS.

Since the BBIssPal uptake into the cells was believed to be mediated by the palmitic acid ligands on the conjugate, the uptake of $^{125}$I-BBIssPal into Caco-2 cells before and after reduction with DTT was studied. Since the presence of serum in the incubation medium had an inhibiting effect on the uptake of the conjugates into the cells, the uptake was studied in serum-free medium. The results are shown in Table 2. The uptake of untreated $^{125}$I-BBIssPal into the cells was 80-fold higher than that of $^{125}$-BBI. The exposure of $^{125}$I-BBI to DTT did not cause a reduction in the uptake. In contrast, the reduction of $^{125}$I-BBIssPal with DTT reduced the uptake of the conjugate in to the cells by approximately 80%. The reduction of BBIssPal with DTT causes the detachment of the palmitic acid from the conjugate. Hence, the uptake of $^{125}$I-BBIssPal was mediated by the hydrophobic palmitic acid ligand.

TABLE 2

| | Uptake (ng BBI/mg of cell protein)/hr | |
|---|---|---|
| | Untreated | DTT-treated |
| BBI | 4.8 ± 0.00 | 5.2 ± 0.00 |
| BBIssPal | 381.7 ± 0.03 | 46.5 ± 0.00 |

The cell uptake of $^{125}$I-BBI, either as the native protein or as BBIssPal was determined before and after reduction with DTT (50 mM) for 5 min at 60° C. and 25 min at 37° C.

Bovine serum albumin (BSA) is known to be a carrier of fatty acids in vivo and contain hydrophobic regions which can tightly bind fatty acids. Since the uptake of $^{125}$I-BBIssPal was reduced in the presence of serum, the possibility that BBIssPal bound to BSA present in FBS was investigated. The cell uptake of $^{125}$I-BBIssPal and $^{125}$I-BBI in the presence of medium containing fat-free BSA or fatty acid-loaded BSA was studied, and the results are shown in Table 3. In the presence of BSA-free medium, the uptake of $^{125}$I-BBIssPal into the cells was 80-fold higher than that of BBI, as was expected from the results obtained in the previous experiments. When defatted-BSA (fatty acid-free BSA) (0.1%) was present in the medium, the uptake of $^{125}$I-BBIssPal was reduced by 82%, whereas the uptake of $^{125}$I-BBI was not affected. In the presence of fatty acid-loaded BSA (0.1%), which was produced by spiking fat-free BSA with a 3-molar excess of palmitic acid, the uptake of $^{125}$I-BBI was again not affected. Therefore, $^{125}$I-BBIssPal binds strongly to BSA and this binding is dependent on the number of fatty acids already bound to BSA.

TABLE 3

| | Uptake (ng BBI/mg of cell protein)/hr | | |
|---|---|---|---|
| | serum free | BSA | BSA/FA |
| BBI | 4.8 ± 0.00 | 4.8 ± 0.00 | 3.9 ± 0.00 |
| BBIssPal | 380.0 ± 0.03 | 69.7 ± 0.00 | 258.9 ± 0.00 |

The uptake experiments were carried out in Dulbecco medium, in the presence and absence of added fatty acid-free BSA (BSA) or fatty acid-loaded BSA (BSA/FA). The results of studies of the uptake of $^{125}$I-BBI, either as the native-BBI or in conjugated form to palmitic or oleic acid, in Caco-2 cells in the presence of serum-free medium were determined as the average ng of BBI internalized ± SEM, n=3. The uptake of $^{125}$I-BBIssPal into the cells was approximately 100-fold higher than that of $^{125}$I-BBI. Similarly, the uptake of $^{125}$I-BBIssOleic into the cells was about 108-fold higher than $^{125}$BBI. The difference between the uptake of $^{125}$I-BBIssPal and $^{125}$I-BBIssOleic were not significant.

Example 4

Biodistribution Assays

Female CF-1 mice, 2 to 3 weeks old, weighing 20–25 g each, with free access to food and water prior to the experiments, were used for the animal experiments. $^{125}$I-BBI (3 mg/kg), as native-BBI or as BBIssPal or BBIssOleic conjugate, was administered to the animals via the tail vein. At 0.5, 3, and 24 hr post-injection, 3 animals from each experiment group were sacrificed and their blood (200 μl), the kidneys, the lungs, and the liver were removed, rinsed in ice-cold PBS, and assayed for accumulated radioactivity. The weights of the organs were recorded and used to adjust the concentration of the conjugates in the organs.

In the ip-biodistribution studies, $^{125}$I-BBI (3 mg/kg), either as the native-BBI or as BBIssPal, was administered into the lower left quadrant of the abdominal cavity of each animal. The animals were then treated in the manner described for the iv.-biodistribution studies.

The results of the biodistribution of BBI and BBIssPal following iv-administration were determined as the % dose accumulated per g organ ± SEM. The results indicated that while BBI was rapidly excreted from the body without attaining high blood levels, BBIssPal was accumulated in the blood at a relatively high level and was apparently more slowly removed from the circulation. The kidney biodistribution results indicated that while BBI was rapidly accumulated in the kidneys, BBIssPal was not. The liver accumulation of BBIssPal was approximately 5-fold higher than that of BBI, and BBIssPal levels remained high in the liver even at 24 hr post-injection. The lung accumulation of BBIssPal was also approximately 2-fold higher than that of BBI, but this result may have been caused by the residual blood present in the organ after its excision. Clearly, BBIssPal was retained longer and at a higher level in the blood and the liver. On the other hand, the kidney clearance of BBIssPal was about 4-fold lower than native-BBI.

The iv-biodistribution of BBI and BBIssOleic were also studied in CF-1 mice. The results were determined as the % dose accumulated per g of the organ ± SEM, n=3, at 0.5, 3 and 24 hr. The biodistribution of BBIssOleic was very similar to BBIssPal. As was observed for BBIssPal, BBIss Oleic had higher blood levels than BBI and was apparently more slowly cleared from the circulation. The blood levels of BBIssOleic were about 4-fold higher than those of BBI at the same time points. The kidney clearance of BBIssOleic was approximately 4-fold lower, and the liver accumulation approximately 4-fold higher than native-BBI. The retention of BBIssOleic in the liver was prolonged, with significant levels of the conjugate present in the liver even at 24 hr post-injection. The lung levels of BBIssOleic were about 2-fold higher than native-BBI levels, but the higher residual blood in the lungs could account for this observation.

The ip-biodistribution of $^{125}$I-BBIssPal in CF-1 mice was determined as the average % dose accumulation per organ ± range at 0.5 hr, 3 hr or 24 hr post-injection. The kidney accumulation of $^{125}$I-BBIssPal was 4-fold lower than that of native $^{125}$I-BBI for the 0.5 and 3 hr time points. At 24 hr, $^{125}$I-BBIssPal levels were higher in the kidneys than $^{125}$I-BBI. The blood level of $^{125}$I-BBIssPal was similar to that of $^{125}$I-BBI at 0.5 hr, 1.5-fold higher than BBI at 3 hr, and approximately 3-fold higher than BBI at 24 hr. The liver accumulation of $^{125}$I-BBIssPal was 1.5-fold higher than $^{125}$I-BBI at 0.5 hr, 2.5-fold higher at 3 hr, and about 4-fold higher at 24 hr. Relatively large amounts of $^{125}$I-BBIssPal were present in the liver and the kidneys at 24 hr.

Example 5

In Vitro Transformation Studies

Transformation assays were carried out using C3H 10T1/2(clone 8) cells according to the published recommendations [Reznikoff, C. A. et al. (1973) *Cancer. Res.* 33, 3239–3249; Reznikoff, C. A. et al. (1973) *Cancer. Res.* 33, 3231–3238]. Stock cultures of mycoplasma-free cells were maintained by passing 50,000 cells per 75 cm$^2$ flask every seven days. Using this schedule, the cells were always passed approximately 2 days before reaching confluence. The stock culture was grown in Eagle's basal medium supplemented with 10% FBS, penicillin (100 units), and streptomycin (100 μg) and used for the transformation assays at passages of 9 to 14. The cells were passed by treating the stock cells with trypsin (0.1%) in PBS for 5 min and quenching the trypsin with 5 ml of the medium. This procedure was adapted to minimize spontaneous transformation in the stock cultures and maximize the plating efficiency in the petri dishes. The FBS stock used in the cultures was pre-screened to ensure that the serum was able to support the expression and the growth of the transformed cells.

For the transformation assays, C3H 10T1/2 cells (1000/dish) were seeded into 60 mm petri dishes and allowed to grow in a humidified 5% $CO_2$ atmosphere in Eagle's basal medium, supplemented with 10% FBS, penicillin (100 units), and streptomycin (100 μg), for 24 hr. Subsequently, the cells were initiated by treatment with 25 μl of the 3-methylcholanthrene (MCA) in acetone stock solution (0.25 mg/ml) to a final concentration of 1 μg/ml of MCA (5 μg/5 ml). The cells were allowed to grow in the presence of the carcinogen or solvent for 24 hr, and the medium in each dish was then replaced with fresh medium containing no carcinogen or solvent. The medium in the dishes was replaced twice per week for the first two weeks of the assay, and thereafter once a week for the remainder four weeks of the assay. In the experiments designed to determine the transformation inhibitory activity of the conjugates, the cells were maintained in the medium containing the conjugates (1 μg/ml) for the first three weeks of the assay; thereafter, the cells were maintained in medium containing no added conjugates.

Six weeks after the carcinogen treatment, the cells were inspected under a microscope for adherence to the culture dishes and were washed with PBS and then fixed in 100% methanol. The fixed monolayers were then stained with Giemsa stain. 20 dishes per group were treated in each experiment. In addition to the test groups, all the transformation assays contained at least three other groups: negative control (not treated with carcinogen or solvent), acetone control (treated with 25 μl of acetone), and positive control [treated with MCA (1 μg/ml) in 25 μl of acetone]. The transformed foci (>3 mm in diameter) in the plates were studied under a microscope and classified according to published guidelines as types I, II, or III [Landolph, J. R. (1985) *Transfomatin assay of established cell lines: Mechanism and Application* (ed. Kakunaga, T., and Yamasaki, H.) IARC Scientific Publications, Lyon, France pp. 185–201]. Briefly, type III foci were dense, multilayered, basophilic, areas of cell growth which stained to a deep blue color with Giemsa and had rough criss-crossed edges. Type II foci were also dense, multilayered, areas of cell growth, but were stained to a purple color with Giemsa and had smoother, more defined edges compared to Type III foci. Type I foci were not scored in the assay.

The plating efficiency (PE) of the cells was also studied in conjunction with each of the transformation assays. To determine the PE of the cells in the different treatment groups, cells (200 cells/dish) were seeded into three 60-mm petri dishes per experiment group and treated in the identical manner as the transformation assay cells. The cells in these assays were terminated at 10 days, fixed with 100% methanol, and stained with giemsa; the colonies of 50 cells or more visible under a microscope were then counted. The plating efficiency is defined as the (number of colonies/number of cells seeded)*100.

The in vitro anti-transformation activity of BBI, BBIss-Pal, and BBIssOleic is shown in Table 4. BBI, either as the free protein or in conjugated form to palmitic or oleic acid, was added to the cultures at 1.0 μg/ml for the first three weeks of the transformation assay period starting immediately after the MCA treatment. MCA-treated cells were exposed to 3-methylcholanthrene, dissolved in 25 /μl of acetone, at a concentration of 1 μg/ml for 24 hr. Acetone-treated cells were exposed to 25 μl of acetone for 24 hr only. The test groups were exposed to MCA for 24 hr and then to the conjugates for the first three weeks of the assay. Untreated cells were exposed to neither MCA nor acetone. Statistical analysis (Chi-square): Group 4 vs 3, $p<0.05$; Group 5 vs 3, $0.05<p<0.1$; Group 6 vs 3, $p<0.05$. Control, untreated cells reached confluence in the dishes about 14-days post-seeding formed well adherent, contact-inhibited monolayers. These dishes contained no transformed foci at the end of the assay period. The acetone treated cells also reached confluence and formed well-adherent monolayers 14 days post-seeding and contained no transformed foci. The MCA-treated dishes, however, contained morphologically transformed foci: 6 out of the 19 dishes scored contained type III foci. The BBI-treated group contained no transformed foci, indicating that BBI could prevent MCA-induced transformation in these cells. The BBIssPal-treated cells contained one type II focus out of the 20 dishes scored in the assay. The BBIssOleic treated cells contained no transformed foci. The PE of all the groups in this assay was between 20% to 25%. As demonstrated in Table 4, both BBIssPal and BBIssOleic retained the original biological activity of BBI.

TABLE 4

| Treatment Group | Plating Efficiency (%) | No. of dishes with transformed foci/No. of dishes | Fraction of dishes containing transformed foci |
|---|---|---|---|
| 1. Controls - untreated | 23 ± 1.5 | 0/20 | 0 |
| 2. Negative controls - acetone treated | 22 ± 2.0 | 0/20 | 0 |
| 3. Positive controls - MCA-treated | 21 ± 3.0 | 6/19 | 0.32 |
| 4. Test-MCA treated + BBI | 24 ± 2.0 | 0/20 | 0 |
| 5. Test-MCA-treated + BBIssPal | 23 ± 3.0 | 1/20 | 0.05 |
| 6. Test-MCA-treated + BBIssOleic | 24 ± 3.5 | 0/20 | 0 |

Example 6

Transport of Single- and Multiple-Conjugates

Studies on transport of apical membrane-bound $^{125}$I-BBIssPal were carried out using transwells and six-well plates. In the six-well plate experiments, $^{125}$I-BBI or $^{125}$I-BBIssPal (10 µg/ml) was incubated with Caco-2 cells in serum-free medium for 1 hr at 37° C. Subsequently, the cells were rinsed three times with ice-cold PBS and then divided into two groups. In the first group the internalization of the conjugates was determined after the trypsinization and isolation of the cells. In the second group, the cells were reincubated with serum-free medium and the release of the conjugates from the cells was chased for 24 hr; medium was removed at hourly intervals and counted for radioactivity. At the end of the chase period, the cells were trypsinized, isolated, and counted for accumulated radioactivity. The total counts in each experiments (medium+cell cpms) were determined, and the % of the total counts released at different times was determined.

In the transwell experiments, the conjugates were incubated with the apical side of the cells for 1 hr at 37° C. The transwells were then rinsed three times with ice-cold PBS and then reincubated with serum free medium. The release of the conjugates into the apical and the basal medium was chased for 24 hr by counting the entire basal or the apical medium at different times. The total counts obtained at the end of the chase period (transwells+media counts were added, and the release of the conjugates (% of total) at different times was calculated. To ensure that the counts obtained in the transwells at 24 hr were due to the presence of the conjugates in the cells and not non-specific binding to the plastic, the transwells were exposed to trypsin for 10 min, rinsed three times with ice-cold pbs, and subsequently counted for accumulated radioactivity.

BBI was modified with 2 or 4 palmitic acids, and the transport was determined in transwells. The cumulative transport of BBI, BBI modified with 4 palmitic acids, and BBI modified with 2 palmitic acids in Caco-2 monolayers were determined as BBI (ng/monolayer) ± SEM, n=3. The order of the transport extent was BBIssPal(4)>BBI>BBIssPal(2). The results of the internalization of the conjugates into the same cells were determined as the ng of BBI internalized per monolayer. As expected, BBIssPal(4) had the highest uptake into the cells, followed by BBIssPal(2) and BBI. The basal media obtained at 24 hr from the transwells was analyzed using a G50 column. As had been observed before, neither BBI nor BBIssPal(4) was transcytosed across the monolayers. However, a small, but significant, amount of the basal media of BBIssPal(2) consisted of intact conjugate. This quantity consisted of between about 10 and about 20% of the total radioactivity present in the basal medium.

Example 7

Skin Absorption of BBIssPal

Freshly-prepared skins from hairless mice were mounted on small rings. To each mounted skin, a 5 µl sample of $^{125}$I-labeled BBI or BBIssPal at a concentration of 0.5 mg/ml was applied to an area of 0.38 cm$^2$. Two pieces of skin were used per treatment. The skins were kept at room temperature (23° C.) in a humidified environment. After 30 minutes, the surface of the skins was first rinsed carefully with PBS; subsequently, the skins were unmounted and soaked twice in 100 ml of PBS. The skins were then blotted with filter papers and counted in a gamma counter. The amount of BBI retained on the skins was calculated using the specific radioactivity of the labeled BBI or BBIssPal. The absorption of BBI and BBIssPal into the mouse skins was 0.14 and 1.6 µg/cm$^2$, respectively. This demonstrates that a more than 10-fold increase of BBI absorption into the skin was achieved when the polypeptide was modified using Pal-PDC.

Example 8

Synthesis of Palmitylated Horseradish Peroxidase (HRPssPal)

Ten milligrams of horseradish peroxidase (molecular weight 40,000; Sigma P 8375) in 0.5 ml of PBS was mixed with 2 ml of SPDP in 0.1 ml DMF at 25° C. for two hours. The reaction was terminated by dilution with 0.5 ml PBS, and dialyzed in 500 ml of PBS at 4° C. After 24 hours, the solution in the dialysis tube was removed, reduced by the addition of 50 µl of 1 M DTT, and separated by using a Sephadex G-50 column. Fractions at the void volume of the column were pooled and mixed with a 10-fold molar excess of Pal-PDC in borate buffer, pH 9.6 at 25° C. for 4 hours. The reaction mixture was then dialyzed exhaustively at 4° C. for 3 days, and the final product was estimated to contain 10 palmitic acid residues per molecule of HRP. The HRP molecules retained approximately 20% of the original enzyme activity.

Example 9

Cellular Uptake of HRPssPal

Confluent monolayers of mouse fibroblasts L929 cells in 6-well culture cluster plates were incubated in serum-free medium with 30 µg/ml of HRP, either as the native form or as the palmitic acid conjugate (HRPssPal). After 1 hour at 37° C., monolayers were washed three times with PBS and then dissolved in 1 ml of 0.05% of Triton-X100. Cell-associated HRP was determined by measuring the enzymatic activity in each cell extract and the results converted to ng HRP per cell monolayer. Results indicated that cellular uptakes of HRP and HRPssPal were 7 and 229 ng HRP per cell monolayer, respectively. Therefore, a 30-fold increase in cell uptake was achieved by modification of HRP with Pal-PDC.

Example 10

Lipidization of Oligonucleotides

An antisense 21mer oligonucleotide which is complementary to the mRNA of monoamine oxidase B is thiolated using the following procedure. The oligonucleotide is mixed with a two-fold molar excess of cystamine in the presence of a water-soluble carbodiimide reagent, EDC. The mixture is maintained at 25° C. for 2 hours and the a two-fold molar excess to cystamine of DTT is added to reduce disulfide bonds.

After separating the oligonucleotide from free cystamine and DTT using a Sepahdex G-25 column, a small amount of the thiolated oligonucleotide is reacted with Ellman's reagent and the concentration of sulfhydryl groups determined using the absorbance at 412 nm (assuming an $\in$ of $1.36 \times 10^4$ $M^{-1}$). Subsequently, the number of sulfhydryl groups per oligonucleotide molecule is determined. The thiolated oligonucleotide is mixed in bicarbonate buffer, pH 8, with Pal-PDC in two-fold molar excess to the number of sulfhydryl groups in the oligonucleotide. The palmitylated oligonucleotide is purified using a Sephadex G-25 column.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A method for prolonging blood and tissue retention of a sulfhydrylgroup containing compound selected from the group consisting of peptides, proteins and oligonucleotides into mammalian cells, said method comprising:

forming from the sulfhydryl-containing compound a compound of general formula VI

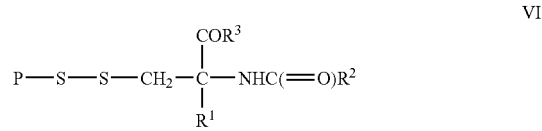

in which P is selected from the group consisting of peptides, proteins and oligonucleotides; $R^1$ is hydrogen, lower alkyl or aryl; $R^2$ is selected from the group consisting of a lipid, —$CH_2CH_2CH(NH_2)CO_2H$ and —$CH_2CH_2CH(NHCO\text{-lipid})CO\text{-lipid}$; and $R^3$ is —OH, a lipid or an amino acid chain comprising one or 2 amino acids and terminating in —$CO_2H$ or —$COR^2$; and administering the compound of general formula VI to the cells;

wherein said lipid is a hydrophobic substituent consisting of 4 to 26 carbon atoms and said lipid together with the attached carbonyl is a fatty acid acyl group.

2. A method according to claim 1, wherein $R^1$ is hydrogen, $R^2$ is a lipid group and $R^3$ is —OH.

3. A method according to claim 1, wherein $R^1$ is hydrogen, $R^2$ is —$CH_2CH_2CH(NH_2)CO_2H$ or —$CH_2CH_2CH(NHCO\text{-lipid})CO\text{-lipid}$ and $R^3$ is —$NHCH_2CO_2H$ or —$NHCH_2CO\text{-lipid}$ in which at least one of $R^2$ and $R^3$ comprises a lipid group.

* * * * *